United States Patent [19]

Sirén

[11] Patent Number: 4,734,283

[45] Date of Patent: Mar. 29, 1988

[54] METHOD OF MAKING A FOOD COMPOSITION CONTAINING INOSOTOLTRIPHOSPHATE AND THE COMPOSITION

[76] Inventor: Matti Sirén, Casa Camboni, Via al Crespo, CH-6596 Gordola, Switzerland

[21] Appl. No.: 788,823

[22] Filed: Oct. 18, 1985

[30] Foreign Application Priority Data

Oct. 23, 1984 [SE] Sweden .................................. 8405295

[51] Int. Cl.$^4$ .......................... A61K 9/68; A61K 31/66
[52] U.S. Cl. ..................................... 424/439; 424/440; 426/3; 426/654; 426/52; 514/103; 514/970
[58] Field of Search ........................ 426/3, 20, 52, 271, 426/7, 496, 589, 590, 615, 654; 424/439, 440; 514/103, 970

[56] References Cited

U.S. PATENT DOCUMENTS 2,723,938 11/1955 Buckwalter et al. ................ 514/103
3,591,665 7/1971 Kimura et al. ............... 252/400.2 X

OTHER PUBLICATIONS

Tomlinson et al., Biochemistry vol. 1, No. 1, pp. 166–171 (Jan. 1962).
Kerr et al., Archives of Biochemistry and Biophysics vol. 96, pp. 347–353 (1962).
Nature, No. 3747, 219–220 (Aug. 23, 1941).
J. Food Sci. vol. 37, 12–13 (1972).
J. Food Sci, vol. 39, 1023–1025 (1974).

*Primary Examiner*—Lionel M. Shapiro
*Attorney, Agent, or Firm*—Scully, Scott, Murphy & Presser

[57] ABSTRACT

A method of making a food composition and the composition containing at least 5 mg of inositoltriphosphate.

36 Claims, No Drawings

METHOD OF MAKING A FOOD COMPOSITION CONTAINING INOSOTOLTRIPHOSPHATE AND THE COMPOSITION

FIELD OF INVENTION

The present invention relates to a method of making an improved food composition containing at least 5 mg inositoltriphosphate ($IP_3$) per 100 g composition and such composition having such content of $IP_3$.

There is an increasing need for counteracting any bad influence of civilization, for instance environmental dangers caused by input of dangerous materials like heavy metals and radiation.

There is also a need for counteracting the hazards of smoking and other bad habits by development of healthy diet and nutrition agents.

Even as early as the year 1900, different researchers had reported the finding of the organic phosphate compound phytic acid, i.e., 1,2,3,4,5,6-hexakis(dihydrogenphosphate)myo-inositol (also sometimes called inositolhexaphosphoric acid) in plants. The content of phytic acid in different plants varies considerably. The content in grain is usually approximately 0.5-2%, with certain exceptions. Polished rice has a level of only 0.1% while wild rice contains as much 2.2% phytic acid. Beans contain about 0.4-2%, oil plants approximately 2-5% and pollen 0.3-2%. The content of phytic acid in the plant varies during the growth period. The content is also influenced by, among other things, the climate.

In the literature there are reports on the presence of inositol pentaphosphate ($IP_5$) and inositol tetraphosphate ($IP_4$) in a few plants. It is further known that phosphate derivates lower than $IP_6$ are formed at germination of grain. For instance the final products at the germination are inositol and phosphate. The use of $IP_6$ has been described in several scientific publications. The majority of the authors of these articles have observed several negative effects on humans and animals when consuming $IP_6$ or substances containing $IP_6$. Feeding dogs with too high an amount of $IP_6$ gives rise for example to rachitis. In humans lack of zinc and as a consequence thereof slower growth of children has been observed. Anemia has been observed mainly in women. Because of the above mentioned negative effects on the mineral balance in humans and animals, attempts have so far been made to reduce the intake of $IP_6$ and its derivatives to a minimum.

Cadmium also has been found to be detrimental to human health. While this metal in general is present in a low level in our environment, the amount of cadmium we are exposed to depends on several factors. Cadmium occurence as well as its availability in the ground varies among different areas, with a relatively high uptake in plants growing in areas with relatively low pH value. By industrial activity, mainly handling of metals, cadmium can be released into the air, ground and water. Cadmium in soil is absorbed by plants and thus can come into the diet of human beings and animals. The most important routes of exposure to cadmium are via smoking, food and, to a certain extent, drinking water.

Cadmium is mainly absorbed in the intestine and through the lungs, although only a small part of the cadmium in the diet is absorbed. The average cadmium intake via food is estimated to be approximately 50 $\mu$g per day in most countries, but the variation is large among different geographic areas and among individuals. Data from smokers show that as much as 50% of the inhaled cadmium can be absorbed. Several investigations show twice as high blood- and organ-levels of cadmium in smokers compared to non-smokers. The excretion of cadmium from the human body is slow and a half-life of 10-30 years has been reported. This means that cadmium is accumulated in the body. The main part, 80-90% of the accumulated cadmium, is bound to a protein, metallothionein, mainly in the liver and kidneys. The formation of metallothionein is induced by metals, mainly zinc and cadmium. The binding of cadmium to metallothionein is very strong and results in a detoxification of cadmium. The remaining cadmium is in the body, i.e. that not bound to metallothiineins, is distributed among the other organs of the body with relatively high levels in the intestine, lungs (especially of smokers), the circulatory system (heart, artery walls, spleen) and glands like the pancreas and prostate.

Among the negative effects, it is known that cadmium can affect the elastin/elastase system of the body. It is also known that cadmium can affect several different enzymes in the body, examples of which are $Na^+$, $K^+$ ($Mg^{2+}$)-ATP-ase and $Ca^{2+}$, $Mg^{2+}$-ATP-ase, which are important in ion transport systems. Further examples are cytochrome-P450-enzymes which hydrolyze steroids, fatty acids, aromatic compounds and toxic compounds. Other important enzymes, which are inhibited by cadmium, are glutathion-peroxidase, and superoxiddismutase, which protect against occurence of peroxidation. Zinc dependent enzymes, such as leucine-aminopeptidase, are also inhibited by cadmium.

Results from a large number of animal experiments obtained over many years show negative effects even at very low levels of cadmium. This would mean that a large proportion of the population is negatively affected, and this is above all valid for smokers. Epidemiological research shows a connection between the presence of cancer, high blood pressure and cardiovascular diseases (for instance, arteriosclerosis, heart infarction, sudden heart death) and the occurence of cadmium in the environment. Exposure to cadmium also seems to be a factor in increasing the risk of age diabetes.

There are also investigations showing that cadmium can have negative effects on the kidneys, lungs (fibrosis, emphysema, cancer), blood vessel walls (fat deposition, arteriosclerosis, vessel wall contraction, elasticity, damage to endothelium), prostacycline production, prostrate, heart (conduction system, force of contraction), placenta, testicles and central nerve system. Cadmium can also induce the formation of free radicals and thereby cause lipid peroxidation, which can be important in the origin of other diseases like rheumatism. Allergies and bronchitis can also be connected with cadmium exposure. The knowledge of the negative influence of cadmium on humans and animals has increased considerably over the last decades.

A very intensive research effort has been made for many years seeking to counteract the above mentioned negative effects of heavy metals, such as cadmium and the negative effects of free radicals which are formed in different ways, for instance by metals such as iron, aluminium and cadmium and by radiation. Of course, also the hazards of smoking have been studied for a long time.

SUMMARY OF THE INVENTION

According to the present invention it has been possible to avoid or at least alleviate the above negative effects observed on humans and animals, by consumption of the special inositolphosphate $IP_3$. Thus, the invention provides a method of making a food composition and the said compositioin containing at least 5 mg of $IP_3$ per 100 g of composition. Generally, it is preferred to use the $IP_3$ in salt form. However, it can also be used in acid form, if desired.

DETAILED DESCRIPTION OF PREFERRED EMBODIMENTS

According to the present invention a food composition having a content of $IP_3$ of at least 5 mg per 100 g composition has been brought about. Very often the $IP_3$ content is at least 20 mg per 100 g composition. Advantageously, the content of $IP_3$ should be within the range of 5-500, preferably in the range of 20-500, more preferably 50-500, 100-500 or 150-500 mg $IP_3$ per 100 g food composition.

The composition can be used as an additive or an intermediate concentrate to increase the $IP_3$ content of other foodstuff products. Then the content of $IP_3$ in said intermediate concentrate should be at least 20 mg per 100 g of the concentrate. Usually, however, the content of $IP_3$ in the concentrate is much higher, advantageous 50 mg-100 g and with preference 75 mg-80 g, 100 mg-80 g, 150 mg-60 g, 200 mg-60 g, 250 mg-50 g or 300 mg-50 g respectively per 100 g concentrate. Preferably, the content of $IP_3$ of the concentrate should be as high as possible.

The intermediate concentrate can be used in many different forms, such as powder, tablets, capsules and granules. However, it is also possible to use it in the form of a liquid, such as an aqueous solution.

The $IP_3$ is preferably selected from the group consisting of D-myo-inositol-1.2.6-triphosphate, D-myo-inositol-1.2.5.-triphosphate, myo-inositol-1.2.3-triphosphate, L-myo-inositol-1.3.4-triphosphate and D-myo-inositol-1.4.5-triphosphate and mixtures thereof. Of these isomers D-myo-inositol-1.2.6-triphosphate is preferred.

Often 20-100, preferably 40-100% by weight of the $IP_3$ content consists of D-myo-inositol-1.2.6-triphosphate.

According to one suitable method for the production of $IP_3$ a material containing $IP_6$ is broken down enzymatically with phytase enzyme. The $IP_6$ can be provided either as pure material or in the form of an $IP_6$ containing source, such as wheat bran. Phytase enzyme can be found for instance in plants, seeds and microorganisms.

By the enzymatic treatment of the $IP_6$ a hydrolysis takes place resulting in a mixture of different lower inositolphosphates, i.e. inositolpentaphosphate ($IP_5$), inositoltetraphosphate ($IP_4$), inositoltriphosphate ($IP_3$), inositoldiphosphate ($IP_2$) and inositolmonophosphate ($IP_1$).

Usually, the hydrolysis is carried out at a temperature of 20°-70° and a pH of 4 to 8. The hydrolysis is suitable stopped when the liberation of about 30-60% of the total ester phosphorus has been achieved. At said stage a high proportion of the desired $IP_3$ isomer of isomers has been formed by hydrolysis of the $IP_6$ containing material.

The mixture of inositolphosphates obtained may hereafter be separated by chromatography to isolate the $IP_3$-containing fraction. Preferably, this is made in a column. If the $IP_3$ fraction contains more than one isomer, these isomers are separated in another subsequent chromatographic separation step.

The $IP_3$ can be obtained as a salt or as an acid thereof. The salt form is preferred, since it is easier to produce in pure and concentrated form than the acid.

The salt form of the $IP_3$ isomer is readily obtainable from the acid form using standard procedures. Thus, there can be prepared salts, such as alkali metal and alkaline earth metal salts, e.g. lithium, sodium, potassium, calcium or magnesium. However, also the zinc salts are very useful as well as the $NH_4^+$ and organic amine salts. Exemplary amines are triethanolamine, diethanolamine, triisopropanolamine, N,N-dimethyl-2-amino-2-methyl-1-propanol, N,N-dimethylethanolamine, tetrabutylamine and cyclohexylamine. Also other salts might be used. Especially preferred salts are those which are physiologically acceptable.

Advantageously, the distribution curve showing the content of the different inositolphosphates has a maximum and preferably the sole maximum for $IP_3$ which means that the content of $IP_3$ is larger than $IP_2$ and/or $IP_4$. Usually the proportion of $IP_3$ is at least 10% of the total amount of inositolphosphates.

Sometimes the composition in addition to $IP_3$ has a content of $IP_4$ and/or inositoldiphosphate ($IP_2$). Then, preferably more than 40% by weight of the total amount of inositolphosphates in the composition consists of $IP_3$, while 30-85% by weight of the remaining inositolposphates consists of $IP_2$ plus $IP_4$. In such a composition the $IP_3$ can consist essentially of D-myo-inositol-1.2.6-triphosphate. However, also other $IP_3$ isomers, especially those mentioned above, can be used in such a foodstuff product.

Depending for instance on the form of the composition the $IP_3$ can be present in salt form or in acid form. The acid form is usually used as a liquid, preferably an aqueous solution. In salt form the $IP_3$ can be used as a dry product or alternatively as a liquid, preferably an aqueous solution.

When $IP_3$ is present as a salt, said salt is generally selected from the group mentioned above.

The invention provides a method of making a food composition, said food being initially substantially free of $IP_3$. The method comprises adding a source of $IP_3$ to the composition in an amount sufficient to provide a final concentration of at least 5 mg $IP_3$ per 100 g of composition.

The source of $IP_3$ can be $IP_3$ as such produced separately or, alternatively, be $IP_6$, $IP_5$ and/or $IP_4$ in the presence of phytase for enzymatic production of $IP_3$.

The term "initially substantially free of $IP_3$" is intended to mean that the food composition produced in the conventional way does not contain a substantial amount of $IP_3$. Thus, the content of $IP_3$ will be less than 3 mg, normally less than 2 mg and most often below 1 mg per 100 g of the composition.

The invention also comprises a method of making a food composition wherein in the materials composing the composition, a content of phytase and of an inositolphosphate selected from the group consisting of inositoltetraphosphate ($IP_4$), inositolpentaphosphate ($IP_5$) and inositolhexaphosphate ($IP_6$), is established, and at at least one stage of the production process, the time and the temperature of the processing as well as the pH-value are controlled to allow an incubation in such a way that a content of inositoltriphosphate ($IP_3$) of at least 20 mg per 100 g composition is obtained.

At said incubation step, at least a portion of the inositolphosphate selected from $IP_6$, $IP_5$ and $IP_4$ is enzymatically broken down to $IP_3$ with phytase enzyme. The proportion of the original inositolphosphate content transformed to $IP_3$ can be regulated within wide limits by varying the production parameters, such as incubation time, temperature and pH as mentioned.

Phytase enzyme may be present in plants or seeds provided they have a content of inositolhexaphosphate. Because of this it may according to the invention, not be necessary in all cases to add the enzyme if a plant or seed product is used as starting material. In the cases where said natural product has too low an enzymatic activity or when $IP_6$, $IP_5$ or $IP_4$ or a mixture of these is used as starting material, a phytase enzyme, for example, from bran can be added.

Yeast can be used advantageously as a source of phytase. Preferably baker's yeast is used.

Swedish baker's yeast produced by Jästbolaget, Sweden, as well as baker's yeast produced by Rajamäki, Finland and Hefefabriken AG, Switzerland have for instance been used according to the present invention. When using yeast according to the present invention it has been established very surprisingly that essentially only one isomer is obtained, namely D-myo-inositol-1.2.6-triphosphate. Of course, the use of yeast is a very valuable procedure if said isomer only is desirable.

During the incubation a hydrolysis takes place at a suitable temperature, usually 20°-70° C., preferably 30°-60° C., and at a pH of 4-8. In order to stop the hydrolysis at the intended level the enzyme may be destroyed or inactivated, for instance by a rapid heating of the hydrolyzed starting material.

The method according to the invention can be modified in different ways, for instance depending on the starting material chosen. The starting material can for instance:

1. have a certain content of $IP_6$, $IP_5$ and/or $IP_4$.
2. have no content of $IP_6$, $IP_5$ or $IP_4$.

At the first alternative above, there are different possibilities to achieve a desired amount of $IP_3$ in the final foodstuff product. For instance the above method of hydrolyzing the inositolophosphates to $IP_3$ by means of phytase can be used.

If the content of $IP_6$, $IP_5$ and/or $IP_4$ is not high enough in the starting material, an addition thereof can be made. In this way the $IP_3$ content of the final product can be increased.

The above method can be used also for the production of an intermediate product with a desired content of $IP_3$, which product can be added to the starting material for the food composition.

The intermediate product can also be introduced at a later stage of the production of the foodstuff product.

Methods of producing $IP_3$ and its isomers as such are disclosed in applicants patent application Ser. No. 788,829 filed on the same day as this application and having the title "Inositoltriphosphate" (applicants file no. 355b).

At the second alternative above, where the starting material has no content of $IP_6$, $IP_5$ or $IP_4$, such an inositolphosphate can be added together with phytase, if phytase is lacking. Then the above hydrolysis method can be used again to give the desired content of $IP_3$ in the final product.

Alternatively, the intermediate product mentioned above can be added to the starting material or at a later stage of the production of the food composition.

At both aforementioned methods, $IP_3$ in concentrated form can be added at a later or final stage of the production of the composition.

In another embodiment of this invention a method of making a food composition is provided in which the composition is initially containing less than about 10 mg of $IP_3$ per 100 g of composition, wherein the content of $IP_3$ is increased to at least 20 mg per 100 g of composition by addition of $IP_3$ or a source thereof or conversion of initially contained inositolphosphate selected from the group consisting of $IP_6$, $IP_5$ and $IP_4$ by enzymatic process. In such method of making a composition according to the present invention, said composition can advantageously be an cereal based material, such as breakfast cereals, cakes, biscuits and bread. The composition can also be selected from the group consisting of sweets, chocolates and chewing gums. Often, quite preferably, the composition is also a vegetable, fruit, beverage, soup or a product based on milk, e.g. yoghurt.

In another embodiment of the invention where the composition initially is containing less than about 20 mg of $IP_3$ per 100 g composition. The content of $IP_3$ is increased to at least 50 mg per 100 g composition in the same way. In a further embodiment of the invention where the composition initially is containing less than about 50 mg of $IP_3$ per 100 g composition. The content of $IP_3$ is increased to at least 100 mg per 100 g composition in the same way.

The content of $IP_3$ in the composition can be varied within wide limits. It is preferred to have a content of $IP_3$ of 20-500, such as 50-500, 100-500 or 150-500 mg $IP_3$ respectively based on 100 g composition. For bakery food the interval is advantageously 20-500, preferably 100-500, and most preferably 150-500 or 200-500 mg $IP_3$ respectively per 100 g dry bakery food. The daily intake of $IP_3$ is at least 10 mg, preferably at least 50 mg.

At the production of a liquid composition according to the present invention, the content of $IP_3$ can also be varied to a large extent. Generally, the content of $IP_3$ is 5-500, such as 10-500, 20-500 or 5-300 mg $IP_3$ per 100 g of the liquid composition.

The liquid composition can for instance be a beverage or soup.

According to the invention a food composition can be provided where in the concertration of $IP_3$ is at least 20 mg per 100 g of dry composition. The $IP_3$ has been added to the composition and/or formed by adding phytase and an inositol phosphate selected from the group consisting of $IP_4$, $IP_5$ and $IP_6$.

In the frame of the invention, bakery products are especially preferred. Thus, a bakery food composition is provided wherein the concentration of $IP_3$ is at least 20 mg per 100 g of dry composition and the degree of hydrolysis of naturally contained $IP_6$ and/or of added $IP_6$ is 20-90% preferably between 40 and 70%. Thus, the ration of inorganic phosphorus to the total amount of phosphorus is at least 20%, preferably at least 40%. At at special bakery food composition the initial content of $IP_3$ is less than 150 mg per 100 g composition and the initial content of $IP_6$ is less than 200 mg per 100 g composition. The content of $IP_3$ in the final composition is then increased by breaking down $IP_6$.

The $IP_3$-isomers mentioned above have the following formulas:

D-myo-inositol-1.2.6-triphosphate of the formula.

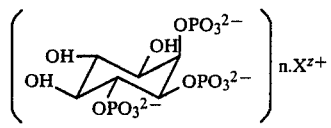

where X is hydrogen, at least one univalent, divalent or multivalent cation, or a mixture thereof, n is the number of ions, and z is the charge of the respectively ion;

D-myo-inositol-1.2.5-triphosphate of the formula

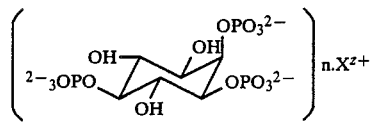

where X, n and z have the above mentioned meaning; myo-inositol-1.2.3-triphosphate of the formula

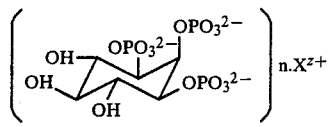

where X, n and z have the above mentioned meaning; L-myo-inositol-1.3.4-triphosphate of the formula

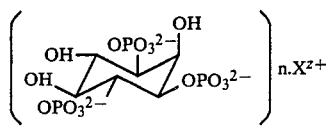

where X, n and z have the above mentioned meaning; and D-myo-inositol-1.4.5-triphosphate of the formula

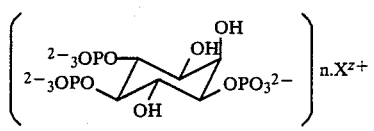

where X, n and z have the above mentioned meaning.

In each of the above formulas n ranges between 6 to 1 inclusively and z ranges from 1 to 6 inclusively. Preferably, n is between 3 to 6 inclusive and z is 3, 2 or 1.

The composition according to the present invention has a good influence on the organism in many ways. However, it is mainly intended to prevent or alleviate conditions created, induced or furthered by heavy metals, especially cadmium or diseases related to such heavy metals.

Also the composition is intended to give a good effect on smokers.

As examples of conditions which the present composition is intended to prevent or alleviate the following can be mentioned; high blood pressure, a cardiovascular disease, emphysema and increased platelet aggregation. However, the composition has a good effect on many other conditions too.

The invention is further explained below in connection with embodiment examples, of which examples 1 and 2 relate to a comparison test where an analysis of inositolphosphates in some commercially available breads and breakfast cereals respectively is made. Examples 3–7 illustrate a method of making bread according to the invention. Example 8 relates to the production of a cake baked on wheat flour with the addition of a calciumsalt of inositolphosphates. Example 9 shows the production of breakfast cereals after addition of a sodiumsalt of inositolphosphates. Example 10 illustrates the production of table-salt by addition of the sodium-salt of D-myo-inositol-1.2.6-triphosphate.

Example 11 illustrates the production of beverages by addition of a sodiumsalt of inositoltriphosphates. Example 12 relates to the production of honey by addition of a sodiumsalt of D-myo-inositol-1.2.6-triphosphate. Example 13 illustrates the production of chocolate by addition of a sodiumsalt of inositolphosphates. Example 14 shows that in blood of rabbits, platelet aggregation caused by an injection of cadmium can be prevented by administration of a diet containing $IP_3$. Example 15 shows the effect of $IP_3$ on the cadmium content in different organs of mice which had got an injection of cadmium. Example 16 shows that $IP_3$ prevents an increase of platelet aggregation caused by smoking. Examples 17 and 18 show that $IP_3$ prevents or reduces the formation of free radicals. Examples 19–24 illustrate hydrolysis of phytic acid in different foodstuff sources. Examples 25–31 show production of $IP_3$ and the separation thereof into different isomers.

EXAMPLE 1

Analysis of inositolphosphates in some commercially available breads

Three commercially aviailable breads, one white bread and two crisp breads, were analyzed for the contents of inositolphosphates with HPLC. The white breads were baked on whole rye flour and whole wheat flour respectively.

A 20 gram quantity of the breads were ground and extracted with 1% hydrochloric acid for two hours at shaking. The suspension was centrifuged and the supernatant was collected.

The supernatant was analyzed with well-defined inositolphosphates and the results were quantified as mg inositolphosphates per 100 g (solid contents).

| Type of bread | (mg/100 g solid content) | | | | |
|---|---|---|---|---|---|
| | $IP_2$ | $IP_3$ | $IP_4$ | $IP_5$ | $IP_6$ |
| White bread | 33 | 2 | 3 | 2 | 2 |
| Crisp bread/whole wheat flour | 37 | 6 | 14 | 71 | 515 |
| Crisp bread/whole rye flour. | 27 | 10 | 13 | 25 | 64 |

The results show that the amount of inositoltriphosphates in the commercially available breads are low.

EXAMPLE 2

Analysis of inositolphosphates in breakfast cereals

Commercially available Corn Flakes ®, Kellog's was analyzed for the content of inositolphosphates with HPLC. The extraction procedure and analysis were the same as described in Example 1.

19 mg $IP_2$ and 2 mg $IP_3$ per 100 g solid content was found. No $IP_4$, $IP_5$ or $IP_6$ could be detected. The $IP_6$ contained in the raw material had almost completely been broken down and the amount of $IP_3$ was very low.

EXAMPLE 3

Variation of the fermentation period for crispbread baked on rye flour

Biologically acidified crisp bread was based on rye flour (1% $IP_6$ content). The dough formulation was: 54.6 g flour, 41.8 g water, 1.3 g salt (NaCl) and 2.4 g of a dough from a preceding doughformulation.

A sour dough consisting of the above 2.4 g of dough from a preciding doughformulation and 40% of the flour and 85% of the water amount was fermented in a first step for 6 hrs before mixing with the other ingredients (flour, water and salt). After mixing, the dough was fermented in a second step before bread forming and baking. The oven temperature was 250° C. Three breads with three different times for the second fermentation period were produced. The breads were ground, extracted and analyzed as described in Example 1. The content of $IP_3$ versus fermentation time was determined as follows:

| Second fermentation time | Amount of $IP_3$ (mg/100 g solid content) |
| --- | --- |
| 30 min | 104 |
| 90 min | 89 |
| 225 min | 78 |

The result shows that an increased second fermentation period resulted in a decrease of $IP_3$ content.

EXAMPLE 4

$IP_3$-content in a bread based on wheat and oat flour

Chemically acidified bread was based on a combination of wheat and oat flour (0.9% $IP_6$ content).

The dough formulation was: 37.7% wheat flour, 17.7% oat flour, 39.5% water, 1.3% salt (50% NaCl and 50% kalciumacetate). 1% sucrose and 2.8% baker's yeast.

After mixing the ingredients the dough was fermented before bread forming and baking. The fermentation period was 90 minutes and the temperature was 37° C. The breads obtained were ground, extracted and analyzed as described in Example 1. The content of $IP_3$ was determined to be 120 mg per 100 g dry bread.

EXAMPLE 5

$IP_3$-content in a bread based on whole wheat flour

A white bread was based on whole wheat flour (0.9% $IP_6$ content). The dough formulation was: 55.9% flour, 38.4% water, 3.5% yeast, 0.6% salt (NaCl) and 1.7% sucrose.

After mixing the ingredients, the dough was fermented before the bread was formed. After an additional fermentation period the bread was baked. The total fermentation period was 60 minutes and the baking temperature was 175° C.

The bread was ground, extracted and analyzed as described in Example 1. The content of $IP_3$ was 70 mg per 100 g dry bread.

EXAMPLE 6

$IP_3$-content in a bread based on rye flour with addition of sodiumphytate

Biologically acidified crisp bread was based on rye flour (1% $IP_6$-content) as described in Example 3 but with the difference that 0.8 g sodiumphytate was added to 100 g dough. The fermentation period was 225 minutes.

The bread was ground, extracted and analyzed as described in Example 1. The amount of $IP_3$ in the bread was 180 mg per 100 g dry bread.

EXAMPLE 7

$IP_3$-content in a bread based on rye flour with addition of calciummagnesiumphytate Biologically acidified crisp bread was based on rye flour (1% $IP_6$-content) as described in Example 3 but with the difference that 1.5 g calciummagnesiumphytate was added to 100 g dough. The fermentation period was 225 minutes. The bread was ground, extracted and analyzed as described in Example 1. The amount of $IP_3$ in the bread was 250 mg per 100 g dry bread.

EXAMPLE 8

$IP_3$-content in a cake based on wheat flour with the addition of a calciumsalt of inositolphosphates A cake was based on wheat flour (0.2% $IP_6$-content). The dough formulation was 60.1% wheat flour, 35.7% water, 0.6% salt (NaCl) and 3.6% yeast.

After mixing the ingredients the dough was fermented. 0.2 g of a calciumsalt of inositolphosphates containing 30% by weight of $IP_3$ was added in 10 ml water per 100 g dough before the cake was formed. After an additional fermentation period the cake was baked in the oven. The total fermentation time was 75 minutes and the baking temperature was 225° C.

The cake was ground, extracted and analyzed as described in Example 1. The amount of $IP_3$ was 60 mg per 100 g dry cake.

EXAMPLE 9

$IP_3$-content in breakfast cereals after addition of a sodiumsalt of inositolphosphates 1000 g commercially available Corn Flakes ®, Kellogg's was sprayed with 10 ml warm (80° C.) aqueous solution containing 50% sucrose and 10% of a sodiumsalt of inositolphosphates (containing 30% $IP_3$). After drying, the breakfast cereals were granned, extracted and analyzed as described in Example 1. The content of $IP_3$ was 30 mg per 100 g dry material.

EXAMPLE 10

Table-salt with addition of sodiuminositoltriphosphate

The sodiumsalt of D-myo-inositol-1.2.6-triphosphate was mixed with table-salt in such a way that a final concentration of 200 ppm $IP_3$ was obtained.

EXAMPLE 11

Beverages with addition of a sodiumsalt of inositolphosphates 20 ml of a 15% aqueous solution of a sodiumsalt of inositolphosphates (containing 40% of $IP_3$) was added to 5 l commercially available Coca-cola ®, Seven-Up ® and orange juice respectively. The final concentration of IP$_3$ in the beverages was found by HPLC to be 190 mg/l.

EXAMPLE 12

Honey with addition of a sodiumsalt of inositoltriphosphates 5 ml of a 20% aqueous solution of the sodiumsalt of D-myo-inositol-1.2.6-triphosphate was added to 50 kg commercially available honey. The final concentration of inositoltriphosphate was determined by HPLC to be 20 mg/kg.

EXAMPLE 13

Chocolate with added IP$_3$

To 1500 g melted chocolate, 6 ml of a 10% aqueous solution of a sodiumsalt of inositolphosphates (containing 30% IP$_3$) was added before lowering the temperature and forming the final chocolate product. The content of IP$_3$ in the chocolate was 110 mg per kg chocolate as determined by HPLC.

EXAMPLE 14

Rabbits (New Zealand white, males) weighing 2-2.5 kg were used. They were fed with a diet free from inositol phosphates, for 10 days before the experiment.

2 hours before the start of the experiment, 50 mg of a sodiumsalt of myo-inositol-1.2.6-triphosphate was mixed into 5 g of the diet for a group of 18 animals. Another group with 12 animals got no addition of inositoltriphosphate.

Time: Treatment 0 minute: Blood sample 1 (9 ml+1 ml 3.8% sodium citrate) taken.
1 minute: Intravenous injection of 4 microgram Cd as CdCl$_2$ in 0.5 ml physiological saline, or 0.5 ml physiological saline respectively.
4 minutes: Blood sample 2 (9 ml+1 ml 3.8% sodium citrate) taken.

TREATMENT OF SAMPLES

The two blood samples from each animal were centrifuged at 1200 revolutions per minute, for 10 minutes, and the plasma with platelets was obtained.

The plasma with platelets from the two samples was analyzed concerning the response to addition of ADP (adenosin diphosphate) in an aggregometer (Chronopar Corp Mod, 440) according to Born (J. Physiol: 67, 1968). The two samples were analyzed simultaneously at the same concentration (1-20 micromolar) of ADP, in the two channels of the instrument.

The principle of this test is that the plasma with platelets is turbid, and has a low transmittance for light. As ADP is added, the platelets aggregate, and form clumps. This results in an increase for transmittance which is quantified by the instrument. The response to ADP was measured in scale units, with 80 scale units representing maximal aggregation. In order to have a maximal sensitivity of the method to pick up changes in platelet reactivity, the ADP dose should cause a response of 5-30 scale units. This was normally achieved with 5 uM ADP, but in some animals a lower or higher dose (1-20 uM) was necessary.

The result of the test is expressed as maximal aggregation in sample 2 (scale unite) minus maximal aggregation in sample 1.

The following results were obtained:

| Oral administration | Injection | No | Change in aggregation from sample 1 to sample 2 (scale unit) |
|---|---|---|---|
| No addition to the diet | Cd | 12 | +2.3 |
| IP$_3$ added to the diet | Cd | 18 | −0.2 |

At the dose used in this experiment, the IP$_3$ prevented the effect of Cd on platelet aggregation.

An increase in platelet aggregation is regarded as one of the most important factors causing cardiovascular diseases e.g. arteriosclerosis, and the ability of IP$_3$ to prevent the aggregation induced by cadmium shows that IP$_3$ is very useful in preventing or allievating such disease.

EXAMPLE 15

Mice weighing 18-20 gram at the start of the experiment were used. During the experiment and for at least seven days before the experiment the mice were fed a semisynthetic diet free of inositol phosphates. The mice were divided in two groups.

They received daily intraperitoneal injections of physiological saline and inositoltriphosphate (IP$_3$) respectively for 9 days. The dose fo IP$_3$ was 5.0 mg/day. The injected volume was 0.2 ml.

On day two of the experiment, 5-10 minutes after the second intraperitoneal injection, all mice received an intravenous injection of 2.5 microcurie of $^{109}$Cd as cadmium chloride in 50 ul of saline. After the last intraperitonial injection the mice were killed and several organs were dissected out and weighed.

Radioactivity in the different organs were measured by counting with a gamma-counter. Radioactivity in the organs of the IP$_3$-treated animals was compared with that of control animals which had been treated with saline for the same period of time. In the results radioactivity in the organs of the animals treated with IP$_3$ is expressed as % of the radioactivity found in controls. The results were as follows:

Organ levels of mice treated with cadmium and IP$_3$ as percent of control levels (controls=100). 15 mice in each group. Said control group had been treated with saline and Cd as mentioned.

| Organ | IP$_3$ |
|---|---|
| Lung | 80 |
| Heart | 77 |
| Aorta | 89 |
| Spleen | 81 |
| Salivary gland | 82 |
| Liver | 100 |
| Kidney | 102 |

The results show that IP$_3$ caused a reduction in cadmium levels in all studied organs except liver and kidney at which letter sites the Cd is believed to be relatively safe.

EXAMPLE 16

The effect of IP$_3$ on platelet aggregation after smoking in humans was studied.

Four young healthy male non-smokers received, on two occasions, a capsule containing 50 mg of IP$_3$ or 50 mg of a placebo. The IP$_3$ used was the Ca-salt of D- myoinositol-1.2.6-triphosphate. Neither subject nor investigator knew whether the subject had received IP$_3$ or placebo.

Two hours after ingestion of the capsule, a blood sample was obtained. The subject then smoked two cigarets in rapid succession. A second blood sample was obtained after smoking. The aggregation responses of the platelets to ADP and collagen in the two samples were determined, using essentially the same procedure as in Example 14. The results are expressed as change in aggregation from the pre-smoking to the post-smoking sample. A positive sigh indicates that aggregation was stronger after smoking.

| Aggregation agent | Concentration of aggregating agent | IP$_3$ | Placebo | Difference between IP$_3$ and placebo |
|---|---|---|---|---|
| ADP | 0.5 mmol | +1.5 | +7.25 | 5.85 |
| " | 1 mmol | −1.5 | +0.25 | 1.75 |
| " | 2.5 mmol | −1.5 | 0 | 1.5 |
| " | 5 mmol | −2.5 | −0.75 | 1.75 |
| Collagen | 0.5 mg | +5.75 | +12.25 | 6.5 |
| " | 1 mg | −8.25 | +1.75 | 10.0 |
| " | 2.5 mg | −3.75 | 0 | 3.75 |
| " | 5 mg | −1.5 | −0.25 | 1.25 |

In the placebo group, smoking caused an increase in aggregation, which was most marked at low concentrations of aggregation agents. In all cases this effect was counteracted by IP$_3$. Thus IP$_3$ prevents increase of platelet aggregation caused by smoking.

EXAMPLE 17

A reaction mixture consisting of 48 mmol KH$_2$PO$_4$, 2 mmol Na-ascorbate, 0.1 mmol H$_2$O$_2$, 0.5 mmol Fe and 1.7 mmol deoxyribose was incubated at 37° C. for 1 hour. Similar reactions mixtures including EDTA 1 mmol or inositol-tri-phosphate (IP$_3$) 1 mmol were similarly incubated. The IP$_3$ used was D-myo-inositol-1.2.6-triphosphate.

After incubation 1.65 ml thiobarbituric acid in 50 mmol NaOH and 1.65 ml 2.8% trichloroacetic acid was added to 2 ml of the reaction mixture. The mixture was heated to 100° C. for 20 minutes and the absorbance at 532 nm was measured with water as a blank.

The experiments were preformed with iron in the form of Fe$^{2+}$ (Fe(NH$_4$)SO$_4$) and Fe$^{3+}$ (FeCl$_3$). The results were as follows:

Production of free radicals catalyzed by Fe$^{2+}$ and Fe$^{3+}$ in the presence of IP$_3$ or EDTA, expressed as absorbance at 532 nm

| Group | Fe$^{2+}$ | Fe$^{3+}$ |
|---|---|---|
| Control | 0.76 | 0.79 |
| EDTA | 2.2 | 1.86 |
| IP$_3$ | 0.46 | 0.43 |

These results show that the formation of free radicals in the reaction mixture was diminished by 40% after addition of IP$_3$. The addition of EDTA had an opposite effect. It strongly increased production of free radicals. Thus IP$_3$ was shown to reduce iron-dependent formation of free radicals.

EXAMPLE 18

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP$_3$ 0.5–5 mM or 0.1 ml H$_2$O |
| 0.1 ml | Fe$^{2+}$ 1 mM or 0.1 ml H$_2$O |
| 0.1 ml | Al$^{3+}$ 4 mM or 0.1 ml H$_2$O |
| 0.1 ml | H$_2$O |

The IP$_3$ was D-myo-inositol-1.2.6-triphosphate. After incubation, 0.5 ml of thiobarbituric acid+0.5 ml 25% HCl was added and the mixture was heated at 100° C. for 15 minutes. 1 ml Lubrol PX 1% (Sigma) was added and lipid peroxidation was measured by measuring the absorbance at 532 nm. The results were as follows:

| Experiment | Concentration, mM | | | Absorbance 532 nm |
| | Fe$^{2+}$ | Al$^{3+}$ | IP$_3$ | |
|---|---|---|---|---|
| 1 | 0.1 | 0 | 0 | 0.367 |
| 2 | 0 | 0.4 | 0 | 0.128 |
| 3 | 0.1 | 0.4 | 0 | 0.896 |
| 4 | 0.1 | 0.4 | 0.5 | 0.367 |
| 5 | 0.1 | 0 | 0.5 | 0.303 |
| 6 | 0.1 | 0 | 0.4 | 0.260 |
| 7 | 0.1 | 0 | 0.2 | 0.297 |
| 8 | 0.1 | 0 | 0.1 | 0.283 |
| 9 | 0.1 | 0 | 0.05 | 0.271 |
| 10 | 0 | 0 | 0 | 0.133 |

Fe$^{2+}$ caused lipid peroxidation (group 1 vs 10). Al$^{3+}$ itself caused no peroxidation (2 vs 10) whereas the combination of Fe$^{2+}$+Al$^{3+}$ caused much stronger peroxidation than Fe$^{2+}$ alone (1 vs 3). Addition of IP$_3$ completely prevented the interaction between Fe$^{2+}$ and Al$^{3+}$ (3 vs 4). In systems with only Fe$^{2+}$, IP$_3$ caused marked reduction in radical formation (1 vs 5–9).

EXAMPLE 19

Hydrolysis of phytic acid in wheat, extraction and analysis of IP$_3$

Ground wheat seeds, 100 g containing 1% myo-inositolhexaphosphate IP$_6$ was incubated in 1000 ml sodiumacetate buffer at pH 5.2 at 35° C. After an incubation period of 30 minutes, the slurry was frozen to −10° C. in order to stop the hydrolysis.

10 g of the frozen material was extracted with 100 ml 0.4M HCl. The suspension was shaken for 1 hr and subsequently centrifuged. The supernatant was collected and neutralized to pH 7 with an aqueous solution of NaOH. A sample of the supernatant was analyzed with HPLC. The analysis method was calibrated with welldefined inositolphosphates. The IP$_3$ content of the extract was 10 mg inositoltriphosphate.

EXAMPLE 20

Hydrolysis of phytic acid in white beans, extraction and analysis of IP$_3$

The same method was used as described in Example 19 except for the difference that 100 g white beans containing 1% myo-inositol hexaphosphate was incubated at 55° C. for 10 hrs.

10 g of the frozen material was extracted with 100 ml 0.4M HCl. The suspension was shaken for 1 hour and subsequently centrifuged. The supernatant was collected and neutralized to pH 7 with an aqueous solution of NaOH. A sample of the supernatant was analyzed with HPLC. The $IP_3$ content of the extract was 5 mg inositoltriphosphate.

EXAMPLE 21

Hydrolysis of phytic acid in soybeans after addition of a phytase source from microorganisms, extraction and analysis of $IP_3$ 300 g soy beans were soaked over night (1.4% $IP_6$ content), peeled and then boiled for 30 minutes. 3 ml water containing about 1 g *Rhizopus oligosporus*, NRRL 2710 was added and the mixture was incubated at 40° C. for 20 hours. 10 g of the mixture was extracted and analyzed by HPLC as described in Example 19. The $IP_3$ content of the extract was 160 mg.

EXAMPLE 22

Hydrolysis of phytic acid in white beans with crude wheat phytase, extraction and analysis of $IP_3$ Ground beans, 100 g, containing 1% myo-inositol-hexaphosphate were suspended in 1000 ml sodiumacetate buffer at pH 5.2. 500 mg crude wheat phytase (from Sigma Chemical Co) was added. The mixture was incubated at 55° C. at shaking. After an incubation period of 12 hrs the slurry was frozen to −10° C. in order to stop the hydrolysis.

10 g of the frozen material was extracted with 100 ml 0.4M HCl. The suspension was shaken for 1 hour and subsequently centrifuged. The supernatant was collected and neutralized to pH 7 with an aqueous solution of NaOH. A sample of the supernatant was analyzed with HPLC. The $IP_3$ content of the extract was 40 mg $IP_3$.

EXAMPLE 23

Content of $IP_3$ in white beans after addition of sodiumphytate and hydrolysis 0.3 gram of sodiumphytate was added to 100 g ground white beans (1% $IP_6$). The mixture was incubated in 1000 ml sodiumacetate buffer at pH 5.2 at 55° C. After an incubation period of 4 hours the slurry was frozen to −10° C. in order to stop the hydrolysis. 10 g of the frozen material was extracted and analyzed by HPLC as described in Example 19. The $IP_3$ content of the extract was 15 mg $IP_3$.

EXAMPLE 24

1.0 kg of rice bran, containing ca 1% inositolhexaphosphate ($IP_6$) was suspended in 10 l sodiumacetate buffer at pH 5° at 25° C. After 4 hours when 50% inorganic phosphorus had been released the slurry was extracted with an addition of 1 l 2M HCl. The suspension was shaken for 1 hour and subsequently centrifuged. The supernatant was neutralized to pH 7 with an aqueous solution of Ca(OH)$_2$. A precipitate was obtained when 5 l ethanol was added. The calciumsalt consisting of a composition of different inositolphosphates was centrifuged, dried and recrystallized. 20 mg of the recrystallized calciumsalt was converted to the acid form by addition of diluted hydrochloric acid and was analyzed by HPLC. The composition consisted of 20% inositoltriphosphate. The rest consisted of other inositolphosphates.

EXAMPLE 25

Hydrolysis of sodium phytate with wheat phytase and fractionation of a mixture of inositolphosphates A 1.6 gram quantity of sodium phytate (from corn, Sigma Chemical Co) was dissolved in 650 ml sodium acetate buffer, pH 5.2. 2.7 gram wheat phytase (EC 3.1.3.26, 0.015 U/mg, from Sigma Chemical Co) was added and the mixture was incubated at 38° C.

The dephosphorylation was followed by determining the inorganic phosphorus released. After 3 hours when 50% inorganic phosphorus was liberated the hydrolysis was stopped by adding 30 ml ammonia to pH 12. A liquid mixture containing inositolphosphates was obtained.

350 ml of the mixture was passed through an ion-exchange column (Dowex 1, chloride form, 25 mm×250 mm) and eluted with a linear gradient of hydrochloric acid (0–0.7N HCl). Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphate etc. Two fractions with the ratio of phosphorus to inositol of three to one were obtained.

EXAMPLE 26

Fractionation of inositoltriphosphates 100 ml of the first fraction obtained in Example 25 with a phosphorus/inositol ratio of three to one was neutralized and precipitated as a bariumsalt after addition of 10% excess of 0.1M bariumacetate solution. 600 mg of the precipitated salt was dissolved in 50 ml 0.18N hydrochloric acid. The solution was separated on an ion-exchange column (Dowex 1, chloride form, 25 mm×2500 mm) with diluted hydrochloric acid as eluent. Aliquots of eluted fractions were analyzed for phosphorus. Three peaks consisting of isomers of inositoltriphosphates can be seen.

EXAMPLE 27

Structural determination of isomers of inositol-triphosphates with NMR

The three peaks obtained in Example 26 were analyzed by H-NMR. Data show that the peaks consist of myo-inositol-1.2.6-triphosphate, myo-inositol-1.2.3-triphosphate and myo-inositol-1.3.4-triphosphate respectively.

The second fraction obtained in Example 25 with phosphorus/inositol ratio of three to one was analyzed by H-NMR. Data show that the fraction consists of myo-inositol-1.2.5-triphosphate.

EXAMPLE 28

Determination of optical isomers of inositol-triphosphates 20 mg of the compounds determined with NMR according to Example 27 to be myo-inositol-1.2.6-triphosphate and myo-inositol-1.3.4-triphosphate were further chromatographed on a chiral column based on acetylated cellulose (20 mm×300 mm from Merck) with a mixture of ethanol and water as eluent. The fractions were analyzed with a polarimeter. As can be seen each compound consists of one optical isomer, D-myoinositol-1.2.6-triphosphate and L-myo-inositol-1.3.4-triphosphate respectively.

EXAMPLE 29

Hydrolysis of sodium phytate with baker's yeast and fractionation of a mixture of inositolphosphates A 0.7 gram quantity of sodium phytate (from corn, Sigma Chemical Co) was dissolved in 600 ml sodium acetate buffer pH 4.6. 50 gram of baker's yeast from Jästbolaget, Sweden (dry substance: 28%, nitrogen content: 2%; phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm×250 mm) and eluted with a linear gradient of hydrochloric acid (0–0.7N HCl).

Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphates etc.

EXAMPLE 30

Structural determination of isomers of inositoltriphosphate

The fraction obtained in Example 29 with a phosphorus/inositol ratio of three to one was neutralized and evaporated before analysis with H-NMR. Data show that the peak consists of myo-inositol-1.2.6-triphosphate.

EXAMPLE 31

Determination of optical isomers of myo-inositol-triphosphate

The same method was used as described in Example 28 with the difference that 10 mg of the compound determined with NMR according to Example 30 was analyzed. As can be seen the compound consists of one optical isomer, D-myo-inositol-1.2.6-triphosphate.

For purposes of further understanding the invention, formulas are given below of some of the IP$_3$-isomers of the invention. Formulas are also given for IP$_6$, IP$_5$, IP$_4$ and IP$_2$.

The lower phosphate-esters of myoinositol are named depending on where the phosphoric acid groups are situated on the inositol ring, with the numbering giving as low position numbers as possible. L and D stand for clockwise and counterclock-wise counting respectively, and are used depending on which result gives the lowest position number. The carbon atom which has an axial phosphoric acid group always has the position number 2. The structural formulae below are simplified to the acid form.

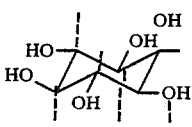

myo-inositol; $C_6H_6(OH)_6$

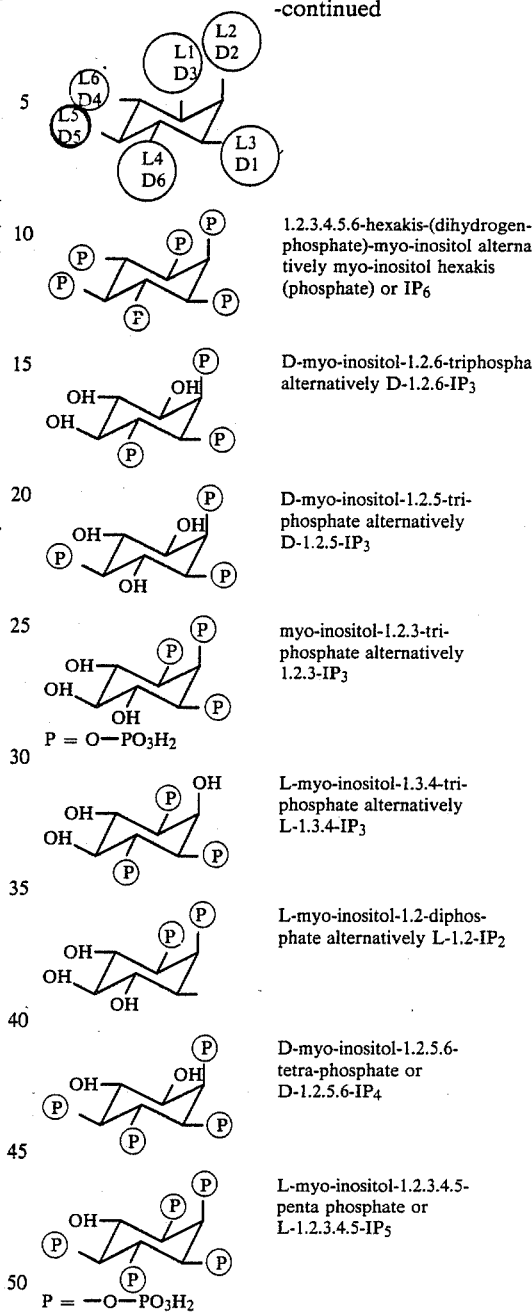

I claim:

1. A method of making a food composition which comprises adding a source of inositol triphosphate (IP$_3$) to a food substantially free of inositol triphosphate in an amount sufficient to provide a final concentration of at least 5 mg IP$_3$ per 100 g. of said food composition.

2. A method according to claim 1, wherein said source is IP$_3$.

3. A method according to claim 1, wherein said source is inositolhexaphosphate (IP$_6$), inositolpentaphosphate (IP$_5$) and/or inositoltetraphosphate (IP$_4$) in the presence of phytase.

4. A method according to claim 1, wherein the source is at least one of the following IP$_3$ isomers, D-myo-inositol-1.2.6-triphosphate, D-myo-inositol-1.2.5-triphosphate, myo-inositol-1.2.3-triphosphate, L-myoinositol-1.3.4-triphosphate or D-myo-inositol-1.4.5-triphosphate.

5. A method according to claim 1, wherein in the materials composing the composition, a content of phytase and of an inositolphosphate selected from the group consisting of $IP_4$, $IP_5$ and $IP_6$ is established and at at least one stage of the production process, the time and the temperature of the processing as well as the pH-value are controlled to allow an incubation in such a way that a content of $IP_3$ of at least 20 mg per 100 g composition is obtained.

6. A method according to claim 1, wherein the composition is solid and the content of $IP_3$ is at least 20 mg per 100 g dry composition.

7. A method according to claim 1, wherein the composition is a cereal based material.

8. A method according to claim 7, wherein the composition is selected from the group consisting of breakfast cereals, cakes and biscuits.

9. A method according to claim 1, wherein the composition is selected from the group consisting of sweets, chocolates and chewing gums.

10. A method according to claim 1, wherein the composition is a vegetable.

11. A method according to claim 6, wherein the composition is bread and the content of $IP_3$ is at least 50 mg per 100 g dry bread.

12. A method according to claim 1, wherein the composition is selected from the group consisting of beverages and soups.

13. A method according to claim 5, wherein the incubation is carried out separately and the $IP_3$ containing product obtained is added to the composition to control the desired $IP_3$ content.

14. A method according to claim 3, wherein the phytase is added in the form of yeast.

15. A method according to claim 5, wherein the temperature ranges between 20° and 70° C. and the pH-value is between 4 and 8 at the incubation step.

16. A method according to claim 1, wherein the $IP_3$ concentration is between 20 and 500 mg per 100 g dry composition.

17. A method according to claim 1, wherein the $IP_3$ concentration is between 50 and 500 mg per 100 g dry composition.

18. A method according to claim 1, wherein the composition is in liquid form and the $IP_3$ concentration is between 5 and 300 mg per 100 g of the liquid composition.

19. A method of making a food composition containing initially less than about 10 mg of $IP_3$ per 100 g of composition wherein the content of $IP_3$ is increased to at least 20 mg per 100 g of composition by addition of $IP_3$ or a source thereof or conversion of initially contained inositolphosphate selected from the group consisting of $IP_6$, $IP_5$ and $IP_4$ by enzymatic processing.

20. A method according to claim 19, wherein the composition is selected from the group consisting of cereal based material, sweets, chocolates, chewing gums, vegetables, fruits, beverages and soups.

21. A method according to claim 19, wherein the content of $IP_3$ is increased to at least 30 mg per 100 g composition.

22. A method of making a food composition, wherein in the materials composing the composition, a content of phytase and of an inositolphosphate selected from the group consisting of $IP_4$, $IP_5$ and $IP_6$ is established and at at least one stage of the production process, the time and the temperature of the processing as well as the pH-value are controlled to allow an incubation in such way that the degree of hydrolysis of $IP_4$, $IP_5$ and $IP_6$ is between 40 and 70% to obtain a sufficient content of $IP_3$.

23. A non bakery based food composition having a content of $IP_3$ of at least 5 mg per 100 g of the composition.

24. A composition according to claim 23 wherein the content of $IP_3$ is at least 10 mg per 100 g of composition.

25. A composition according to claim 23, wherein the composition is selected from the group consisting of sweets, chocolates, chewing gums, vegetables, fruits, beverages and soups.

26. A composition according to claim 23, wherein the $IP_3$ is at least one of the following isomers, D-myo-inositol-1.2.6-triphosphate, D-myo-inositol-1.2.5-triphosphate, myo-inositol-1.2.3-triphosphate, L-myo-inositol-1.3.4-triphosphate or D-myo-inositol-1.4.5-triphosphate.

27. A bakery food composition comprising a bakery food and inositol triphosphate ($IP_3$), said $IP_3$ present in a concentration of at least 20 mg per 100 g of said composition.

28. A composition according to claim 27 wherein the concentration of $IP_3$ is at least 30 mg per 100 g of dry composition.

29. A composition according to claim 27 wherein the bakery food is selected from the group consisting of bread, breakfast cereals, biscuits and cakes.

30. A composition according to claim 27, wherein the $IP_3$ is substantially D-myo-inositol-1.2.6-triphosphate.

31. A composition according to any of claims 23–27, wherein the $IP_3$ is a hydrolysate product derived from an inositolphosphate selected from $IP_4$, $IP_5$ and $IP_6$ in which the distribution curve showing the content of the different inositolphosphates has a maximum for $IP_3$.

32. A composition according to claim 31, wherein the content of $IP_3$ is more than 40% by weight of the total amount of inositolphosphates and 30 to 85% by weight of the remaining inositolphosphates consist of $IP_2$ and $IP_4$.

33. A composition according to claim 23, in concentrate form which comprises $IP_3$ in a food acceptable extending agent.

34. A food composition, wherein the concentration of $IP_3$ is at least 20 mg per 100 g of dry composition, and $IP_3$ has been added to the composition and/or formed by adding phytase and an inositolphosphate selected from the group consisting of $IP_4$, $IP_5$ and $IP_6$.

35. A composition according to claim 24 wherein the content of $IP_3$ is in the range of between 20 and 500 mg per 100 g of composition.

36. A composition according to claim 28 wherein the concentration of $IP_3$ is in the range of 50 to 500 mg per 100 g of dry composition.

* * * * *